United States Patent [19]

Bonnand et al.

[11] Patent Number: 5,008,996
[45] Date of Patent: Apr. 23, 1991

[54] MACHINE FOR REMOTELY LINING THE INSIDE OF A HEAT EXCHANGER TUBE END WITH A SLEEVE

[75] Inventors: Christian Bonnand, Bachy;
Dominique Mascart, Toufflers;
Philippe Druelle,
Gournay-sur-Marne, all of France

[73] Assignees: Stein Industrie, Velizy-Villacoublay;
Electricte de France, Paris, both of France

[21] Appl. No.: 342,826

[22] Filed: Apr. 25, 1989

[30] Foreign Application Priority Data

Apr. 25, 1988 [FR] France ............................... 88 05448

[51] Int. Cl.$^5$ ............................................. B23P 15/26
[52] U.S. Cl. ...................................... 29/727; 29/723;
29/890.031; 29/890.043
[58] Field of Search ................ 29/157.3 C, 157.3 V,
29/727, 723, 157.4, 402.16, 523, 890.031,
890.043; 376/260

[56] References Cited

U.S. PATENT DOCUMENTS

| | | |
|---|---|---|
| 3,934,731 | 1/1976 | Muller et al. |
| 4,329,769 | 5/1982 | Glatthorn ........................ 29/727 |
| 4,494,907 | 1/1985 | Coussau et al. |
| 4,571,821 | 2/1986 | Pirl et al. ....................... 29/727 |
| 4,586,250 | 5/1986 | Cooper, Jr. et al. ............... 29/727 |
| 4,639,994 | 2/1987 | Cooper, Jr. et al. ............ 29/727 X |
| 4,653,164 | 3/1987 | Cooper, Jr. et al. ............... 29/723 |
| 4,685,186 | 8/1987 | Glatthorn ................. 29/157.3 R X |
| 4,688,327 | 8/1987 | Cooper, Jr. et al. ............ 29/727 X |
| 4,829,648 | 5/1989 | Arzenti et al. .................. 29/157.4 |

FOREIGN PATENT DOCUMENTS 2598950  11/1987  France .

Primary Examiner—Howard N. Goldberg
Assistant Examiner—D. Cuda
Attorney, Agent, or Firm—Sughrue, Mion, Zinn, Macpeak & Seas

[57] ABSTRACT

A machine for remotely lining the inside of a heat exchanger tube end (13) received in a tube plate (14). The machine includes a flexible tube (15) connecting a push-pull device to a motorized unit (16) for driving tools used for fixing the sleeve in the heat exchanger tube. The machine also includes a tool loader (25, 26) at the head of a cable (20) which is driven by the push-pull device and means for applying the end of the flexible tube to the end of any of the heat exchanger tubes which may need lining. The motorized unit (16) includes two superposed fluted hubs (30, 33) one of which is driven by a low speed electric motor while the other is driven by a high-speed pneumatic motor.

15 Claims, 10 Drawing Sheets

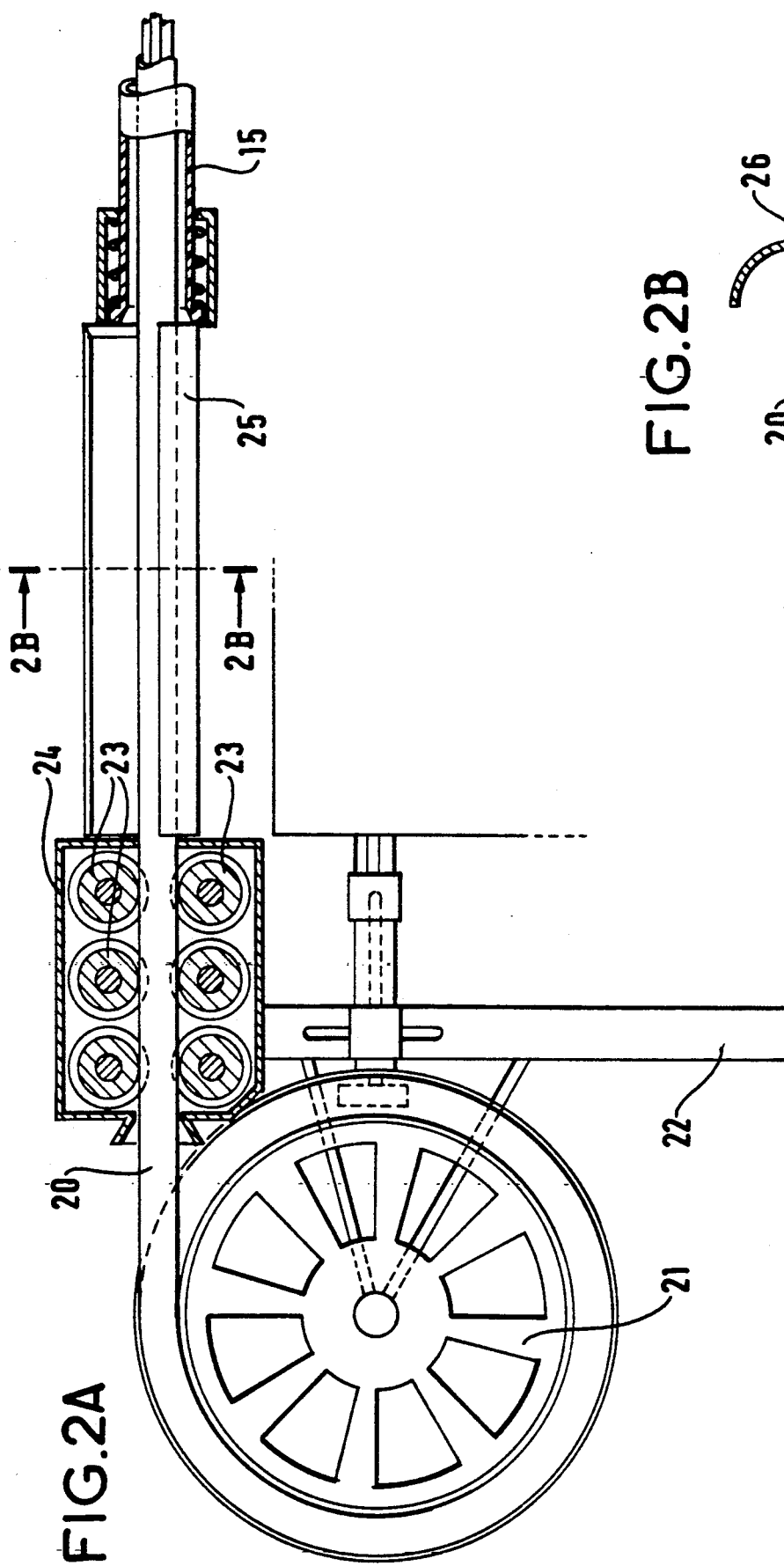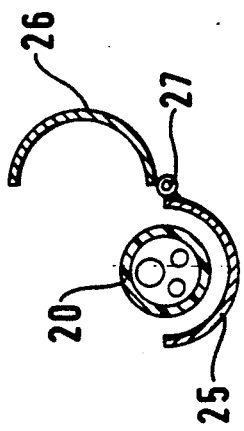

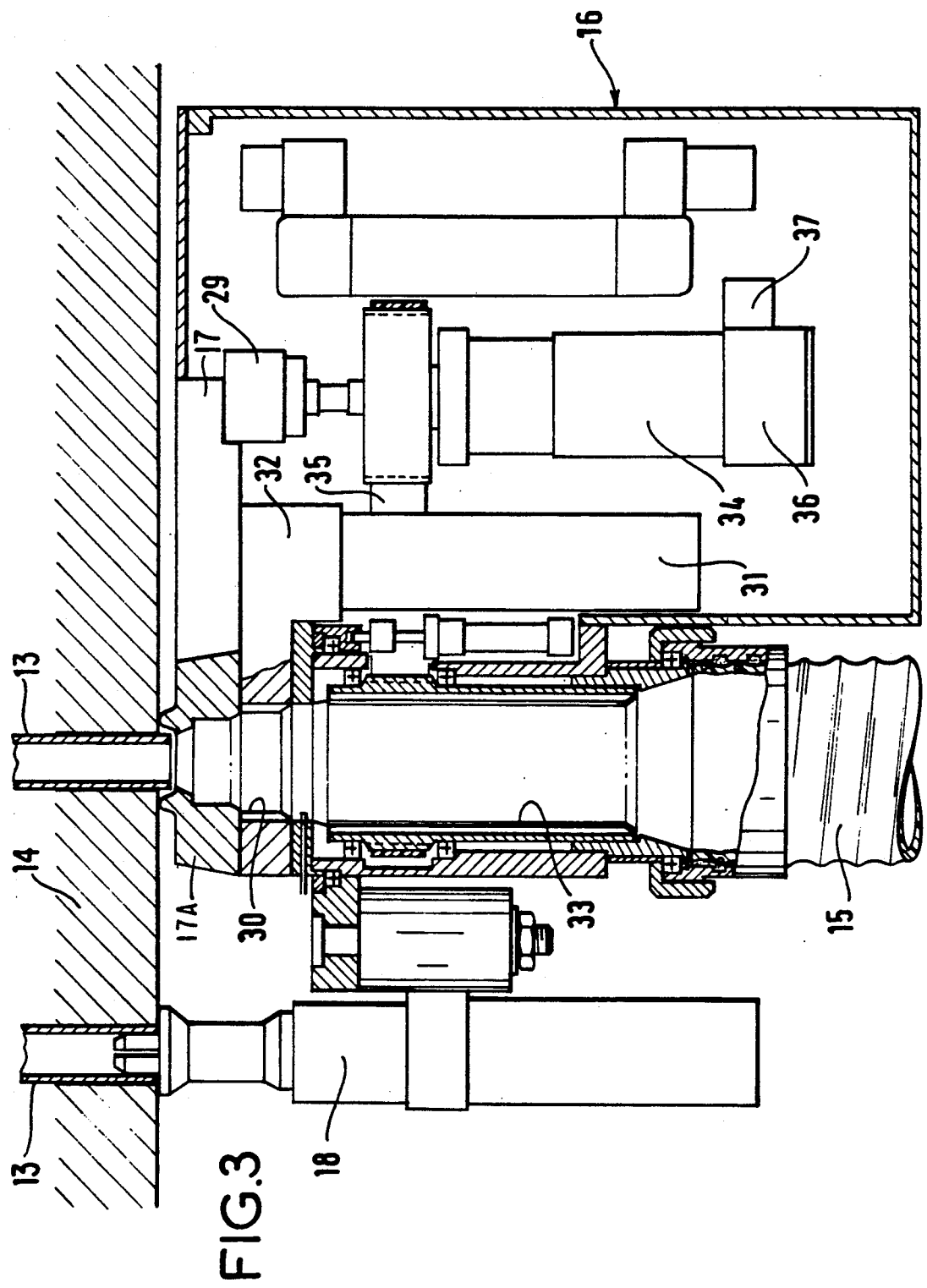

FIG.8A
FIG.8B
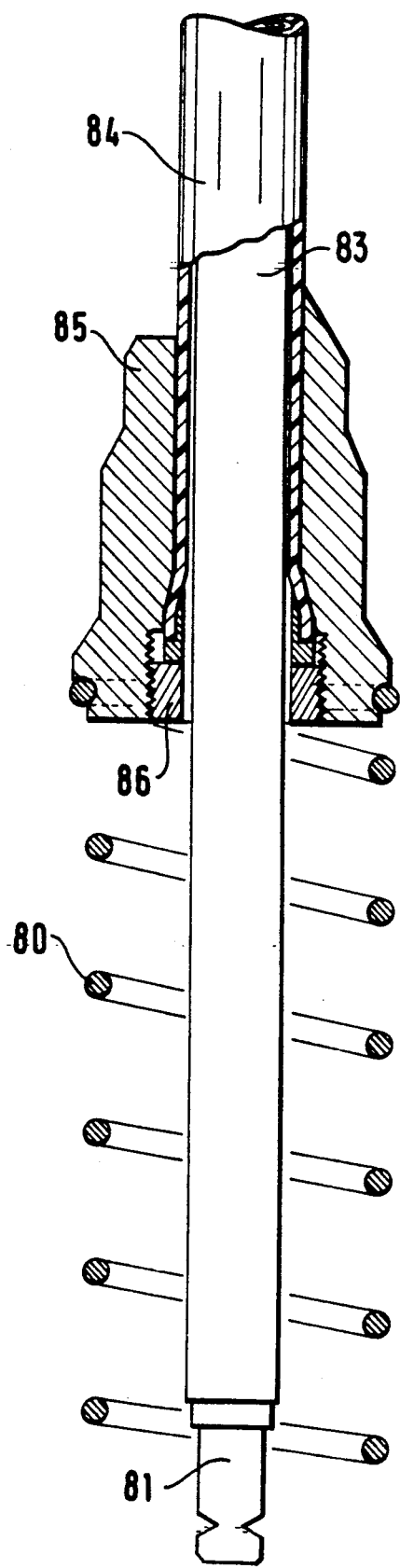
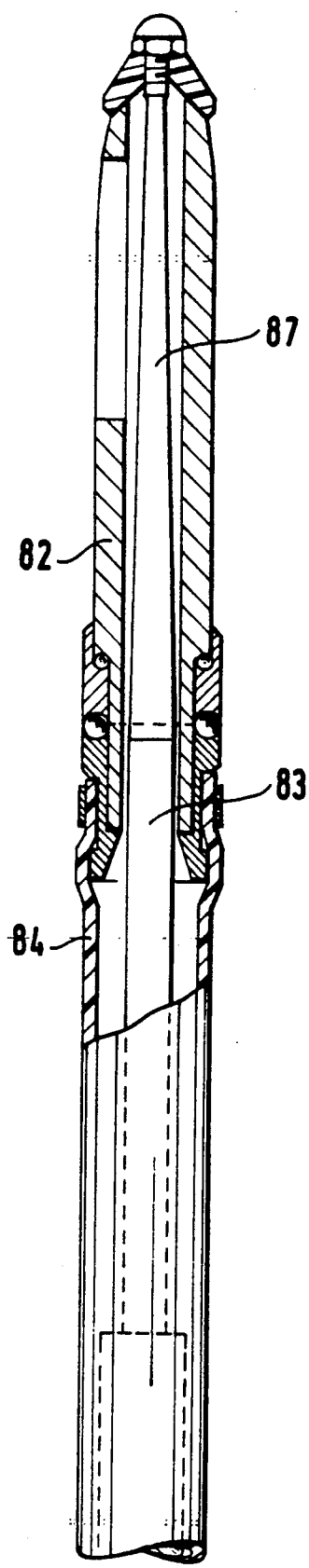

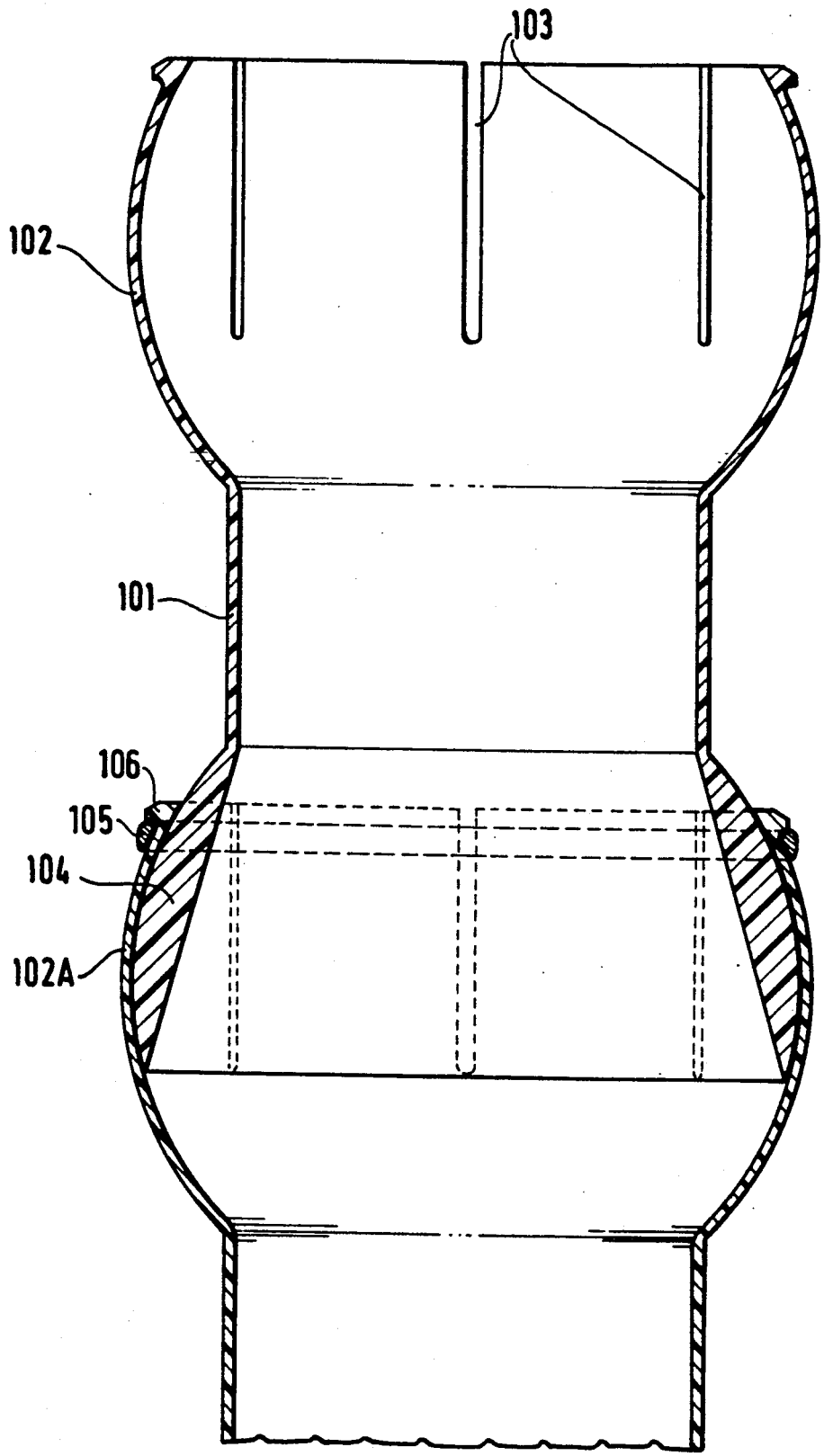

MACHINE FOR REMOTELY LINING THE INSIDE OF A HEAT EXCHANGER TUBE END WITH A SLEEVE

The present invention presents a machine for remotely lining the inside of a heat exchanger tube end with a sleeve, said end being mounted in a tube plate with a water box being disposed beneath the tube plate, the water box being accessible from the outside via a manhole, the machine operating by a method including inserting a sleeve into the end of a tube, diametrically expanding the sleeve in a zone inside the tube plate and in a zone beyond the tube plate, then expanding the sleeve by rolling and then welding the sleeve in each of its expansion zones, said machine including a push-pull device outside the water box, with a flexible tube connecting the push-pull device to a motorized unit for driving the sleeve-fixing tools, a tool loader at the head of a cable driven by the push-pull device, and means for bringing the end of the flexible tube level with the end of each of the tubes in succession.

It is particularly applicable to lining the inside of steam generator tube ends in pressurized water nuclear reactors in order to repair cracking or corrosion close to the ends of such tubes.

BACKGROUND OF THE INVENTION

French patent document FR-A-2 598 209 describes a device for remotely lining the end of a steam generator tube in a pressurized water nuclear reactor, which tube is fitted into a thick tube plate by tube expansion, with a water box being located beneath the tube plate and being accessible from the outside by means of an inspection hatch. The method used comprises inserting a sleeve into the end of the tube, expanding the sleeve diametrically in two zones in the vicinity of said end, one of said zones being inside the thickness of the tube plate and the other beyond said tube plate, then expanding the sleeve by rolling in each of the expansion zones in order to lock it into place, said device including a handling member provided with an arm whose end can be placed beneath the tube plate and in vertical alignment with any one of the tubes, and a tubular guide element fixed to the end of the arm in a direction perpendicular to the tube plate, a flexible tube having one of its ends near the tube plate fixed to the tubular guide element and passing through the manhole so that its opposite end lies outside the water box, a loading and handling assembly connected to the end of the flexible tube which is outside the water box for the purpose of displacing a sleeve inside the flexible tube with a hydraulic expander being located inside the sleeve and fixed for displacement purposes to the end of a flexible tubular cable fed with a hydraulic fluid under pressure, and a handling and expansion assembly including tooling for expanding a tube by rolling fixed to the end of a flexible tubular element associated with a handling member disposed outside the water box for the purpose of displacing it inside the flexible tube, and connected to drive members by means of a flexible element passing through the flexible tubular element.

However, such a device cannot displace any type of tool and nor can it verify that the various operations, in particular the operation of expansion by rolling, are performed properly. When a sleeve is to be expanded by rolling inside the tube beyond the tube plate under control of the drive members of the handling member from outside the water box and by means of the flexible element passing through the flexible tubular element, there is no way of checking that the motion imparted by the drive members is properly transmitted to the expansion tool, nor is there any way of verifying that the expansion tool rotates through the required number of turns to ensure that the sleeve is fixed inside the tube in sealed manner. Nor is it possible to monitor the couple exerted by the tube expanding motor disposed inside the water box for the purpose of expanding tubes inside the tube plate by rolling. Finally, displacements of the flexible tube vary its elongation such that the positions of the tools at the end of the flexible tubular cable are not known accurately.

The object of the present invention is to ensure that the various operations of cleaning the insides of the tubes, of installing and docking sleeves in the tubes, of welding the sleeves in the zone in which they have been docked, of monitoring the welds, of expanding portions of the tubes by rolling and of heat treating the welded and expanded zones are performed with great accuracy and preferably while constantly monitoring the progress of said operations, thereby obtaining good sealing at the ends of the tubes fitted with internal linings.

SUMMARY OF THE INVENTION

In the machine of the invention the motorized unit for driving the tools comprises two superposed fluted hubs one of which is driven by a low speed electric motor and the other of which is driven by a pneumatic motor having a high speed of rotation.

It preferably includes at least one of the following features:

the pneumatic motor is mounted on a bearing and is provided with a force cell for measuring its couple;

the tools for tube expansion by rolling are driven by the fluted hub of the pneumatic motor engaging fluted drive jaws on the spindles thereof, with the flutes therein allowing the jaws to slide axially;

the tools for tube expansion by rolling are provided with springs for maintaining their spindles in a position which is clearly separated from the tool cage when at rest, which springs are compressible by the thrust cable;

the tool for cleaning the insides of the tubes comprises a flexible brush rotated by the pneumatic motor and moved in translation by a nut and screw system, the screw being provided with a central bore through which particles detached by the brush are sucked, and the thrust cable of the flexible brush is itself provided with an internal passage for removing said particles;

the tool for placing the sleeve inside the tube includes a skin of plastic material which is inflatable under the effect of hydraulic pressure in an internal chamber;

the skin is carried by a support having a retractable cone provided with a contact for detecting that the sleeve is in the proper position inside a tube;

the skin is connected to a metering pump for delivering very small volumes and to means for comparing the increase in pressure after each pump stroke with the increase after preceding pump strokes;

the tool for docking the sleeve against the tube inside the tube plate is a tube expander having rollers parallel to its spindle, and provided with a projection for localized deformation of the sleeve, being driven by the pneumatic motor via a screw and nut system;

the tool for docking the sleeve against the tube beyond the tube plate is a tube expander having sloping rollers, or a skin whose volume is controlled as a function of the internal hydraulic pressure so as to go beyond the elastic limit of the tube;

the tools for welding the sleeve to the tube are flexible lances driven in rotation by the electric motor and connected to ducts for feeding them with water, gas, and electricity, said ducts running inside the thrust cable;

it includes cells located close to the motorized unit for driving the tools and serving to detect the presence of the tools and to count the numbers of rotations of the tools;

it includes ultrasonic probes for monitoring the welds, said probes being rotated by the pneumatic motor and being moved axially by a screw and nut system connected to the pneumatic motor, said tools serving to pick up the interface echoes between the sleeve and the tube and the background echo on the tube;

its flexible tube is constituted by an assembly of cylindrical elements having ends which interfit in one other; and its flexible tube is constituted by an assembly of interfitting elements having ball-and-socket forming ends.

BRIEF DESCRIPTION OF THE DRAWINGS

An embodiment of the invention is described by way of example with reference to the accompanying drawings, in which:

FIG. 2A is a fragmentary section view through the member for pulling and pushing the control cable from outside the water box, and FIG. 2B is a section on line 2B—2B of FIG. 2A;

FIG. 3 is a fragmentary section through the motorized unit disposed in the proximity of the tube plate;

FIGS. 8A and 8B are section views through an expansion tool for final expansion of the sleeve inside the tube;

FIG. 10 is a section through a component having ball-and-socket ends for constituting a flexible tube for inserting tools into the water box.

DETAILED DESCRIPTION

Figure 1:
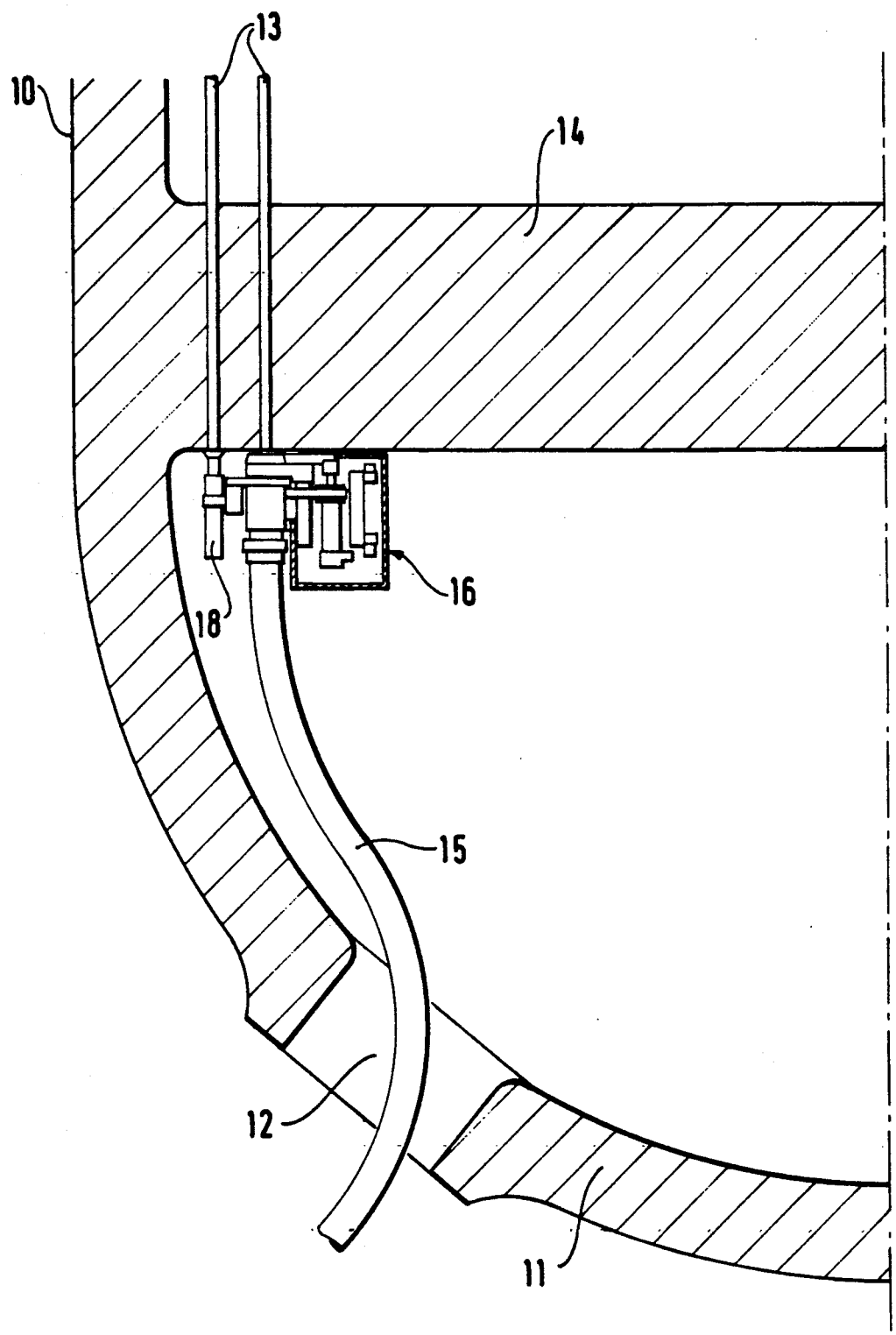
FIG. 1 is an overall section view through that portion of the device located inside the water box.

In FIG. 1, the heat exchanger 10 is terminated by a water box 11 pierced by a manhole 12. The tubes 13 of the heat exchanger pass through a thick tube plate 14. The sleeves for lining the insides of the tube should be inserted into the ends of the tubes up to a certain distance beyond that face of the tube plate which is furthest from the water box. The various operations are performed by means of a motorized unit 16 shown in greater detail in FIG. 3. The tools are conveyed to the motorized unit via a flexible tube 15 which passes through the manhole. A leg 17 holds a ring 17A which guides the flexible tube so as to be vertically aligned with the tube 13 to be lined. The motorized unit is held in position at any given moment in front of the tube to be lined by a carrier member at the end of a positioning arm (not shown), and it is fixed to the tube plate by means of members for locking in the ends of other tubes, e.g. the member 18.

FIGS. 2A and 2B show the push-pull member which is outside the water box and thus accessible without danger. It is intended to pull or push a cable 20 which is wound on a drum 21 supported by a beam 22. Motor driven wheels 23 disposed in a box 24 are used for pulling or pushing the cable. A cylindrical loader 25 is disposed between these wheels and the end of a flexible tube 15, the loader is open in both longitudinal directions and it has a lid 26, FIG. 2B, pivotally mounted about an axle 27. The outside diameter of the loader is slightly less than the inside diameter of the flexible tube 15 and the loader is used for inserting tools which are fixed to the end of the cable 20.

The motorized unit shown in FIG. 3 is held in position in front of the tube 14 to be lined by means of a carrier member of conventional type and visible in part (e.g. a robot arm). As in FIG. 1, a member 18 can be seen for locking into the end of an adjacent tube 13A, with other locking members being omitted from the drawing.

This unit has two superposed fluted drive hubs, namely a top hub 30 and a bottom hub 33. The top hub 30 is driven by an electric motor 31 via a belt 32. The bottom hub 33 is driven by a pneumatic motor 34 via a belt 35. It is mounted on a bearing 36. A force cell 37 monitors the couple transmitted to the hub 33. Encoders such as 29 specify the number of spindle rotations to be given to the tube expanding rollers or the number of screw turns or fractions of screw turns to be imparted to the welding lances or to the probes for monitoring the welds by means of ultrasound, as described below.

Infrared cells (not shown) serve to detect the presence of tools in the motorized unit and to count the number of rotations of the cage for the tube expansion rollers or the number of rotations of the nut for tools driven by a nut and screw member.

Figure 4:
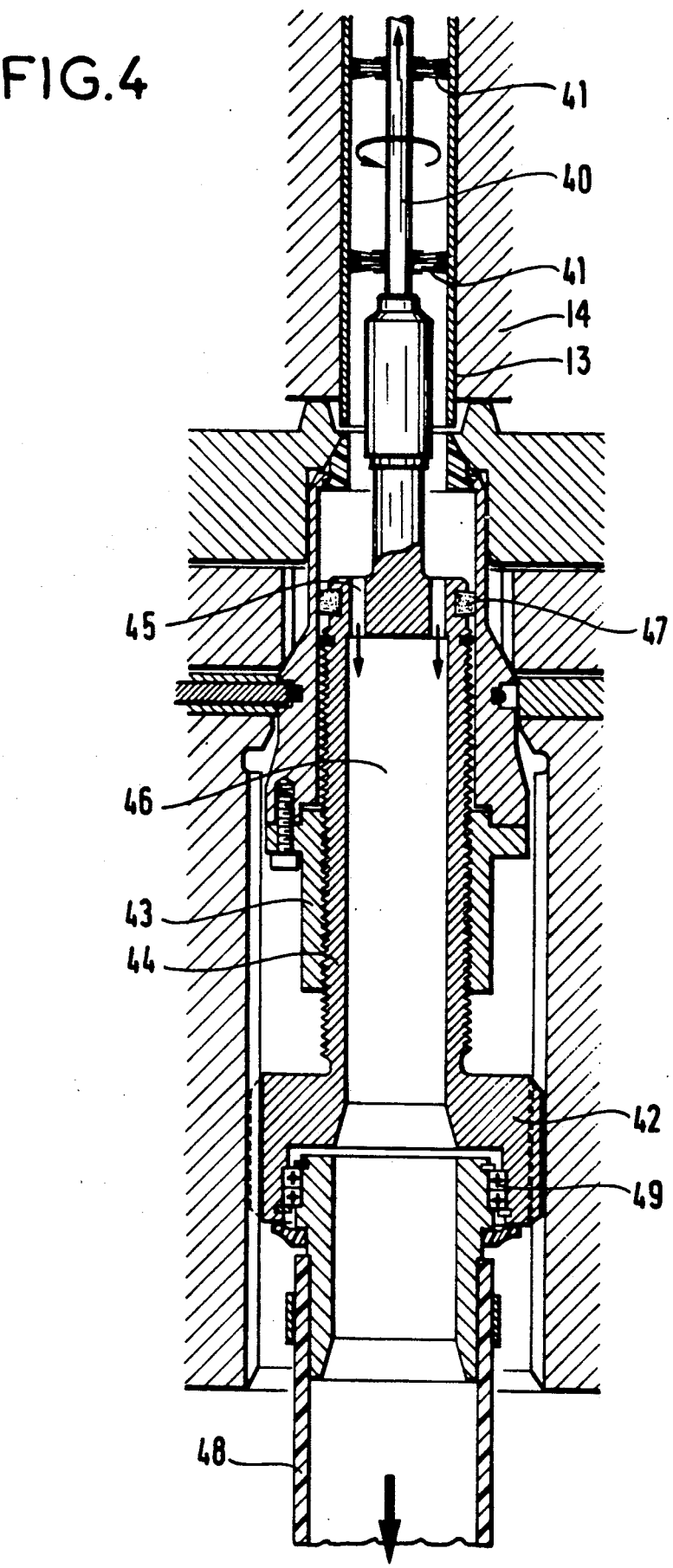
FIG. 4 is a section through the member for cleaning the insides of the tubes.

The tooling for cleaning the insides of tubes is shown in FIG. 4. It comprises a rod 40 carrying a flexible brush 41 which is rotated by the pneumatic motor via a gear wheel 42 and which is moved axially by a system comprising a nut 43 and a hollow screw 44 connected to the pneumatic motor. Particles detached from the inside surface of the tube by the brush are sucked up via channels 45 and the inside bore 46 through the screw, with a peripheral pad 47 preventing the particles from penetrating into the screw thread. The particles continue to be sucked along the inside of the plastic thrust cable 48 (e.g. made of polyethelene) with the gear wheel 42 rotating on the end thereof by means of a ball bearing 49.

Figure 5A:
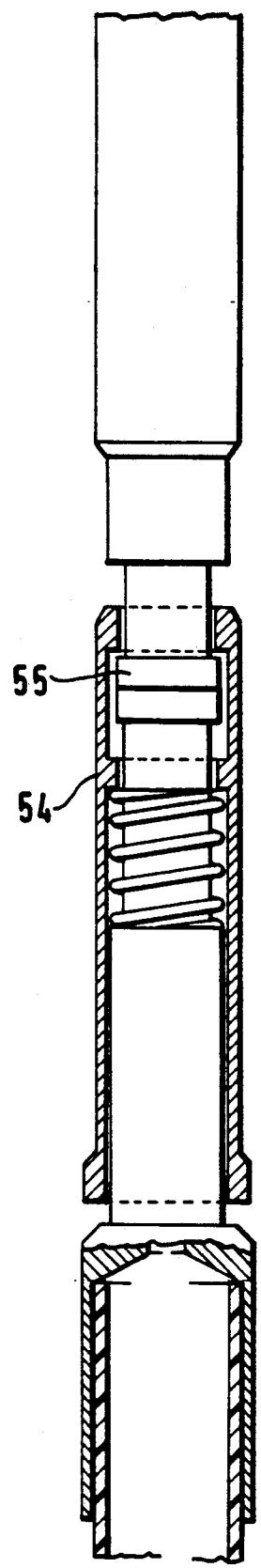
FIGS. 5A, 5B, and 5C are fragmentary sections through the member for temporarily fixing a sleeve inside a tube.
Figure 5B:
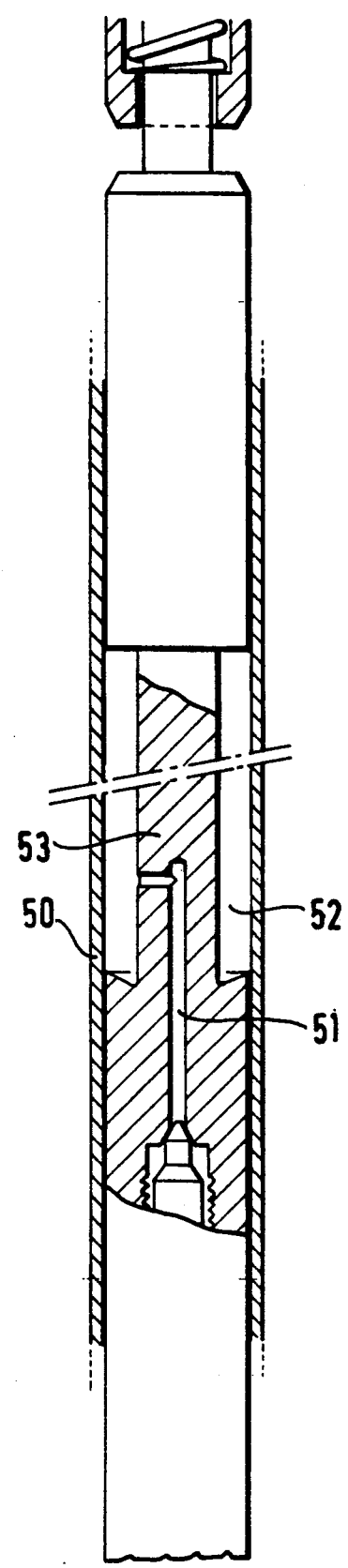
Figure 5C:
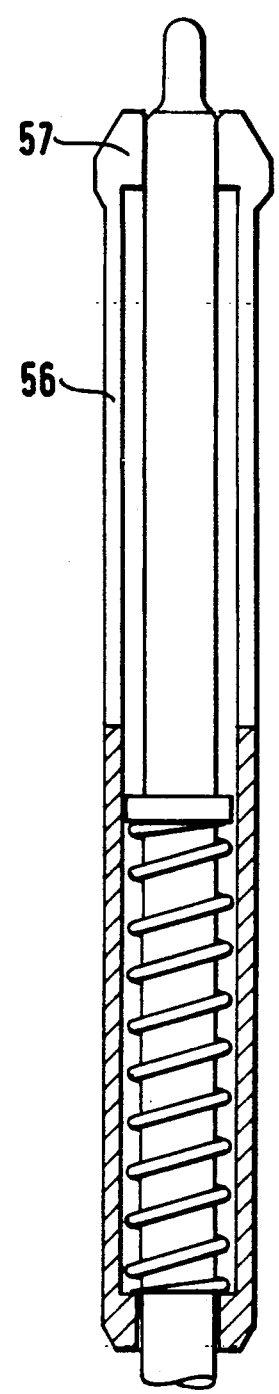

FIGS. 5A, 5B, and 5C show an inflatable skin for temporarily fixing a sleeve inside a tube prior to docking and welding. The skin 50 is made of polyurethenane and is inflatable by distilled water raised to a pressure which may be as much as 1500 bars and delivered via duct 51 into a cavity 52 between the skin and the rod 53. The pressure thus deforms the sleeve and fixes it temporarily against the surface of the tube to be repaired. An electrical contact 55 supporting the skin 54 serves to indicate, by closing, that the sleeve is properly positioned for insertion purposes. A portion of this skin support is flexible so as to enable the sleeve to be inserted into the peripheral zone of the tube plate where the wall of the water box impedes access to the tubes.

The skin support is provided close to its leading end with a clamp 56 which is retracted when traction is applied thereto. The leading cone 57 of the clamp facilitates guidance of the sleeve inside the flexible tube and insertion of the sleeve into the tube to be repaired.

Figure 6A:
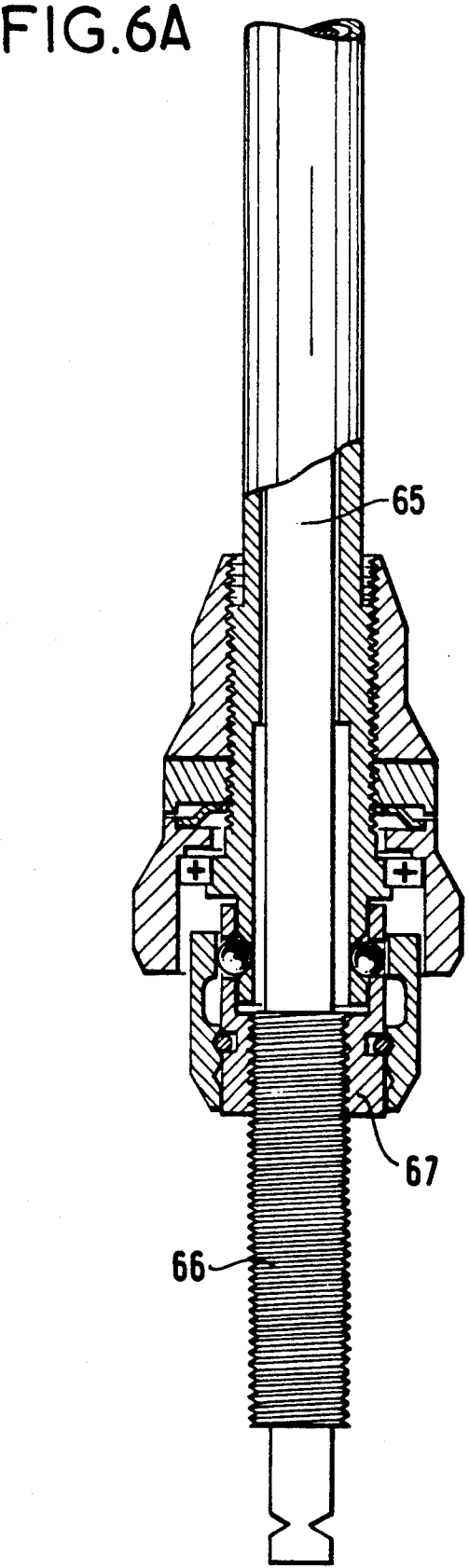
FIGS. 6A and 6B are sections through a docking expander tool having rollers parallel to its spindle.
Figure 6B:
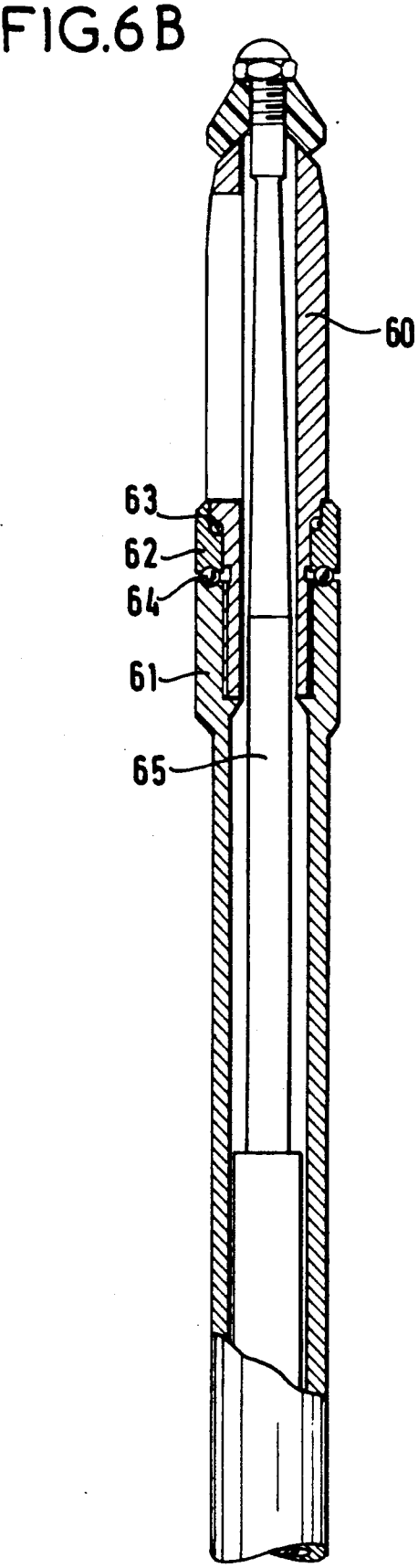

FIGS. 6A and 6B show a tube expander tool having parallel rollers which is used for docking the sleeve against the inside surface of the tube inside the tube plate in order to fix the sleeve in place prior to welding. The rollers 60 have respective projections which give rise to highly localized deformation of a sleeve by rotating relative to the spacers 61 of their cages by virtue of ball abutments 62 and ball bearings 63, 64. The spindle 65 is advanced by engagement of a threaded portion 66 thereof in a dismantleable nut 67.

The sleeve is docked in the tube beyond the tube plate by controlled deformation of the sleeve and of the tube to be repaired while counting the number of revolutions of the spindle of a conventional type of tube expansion tool having sloping rollers (not shown) or by controlling the volume of a deformable skin (also not shown) by means of a computer and as a function of internal water pressure injected by a metering pump (not shown). The change in slope in the plot of volume as a function of pressure corresponding to the elastic limit of the metal being exceeded is observed by injecting successive small volumes of water (70 mm$^3$ to 200 mm$^3$) into the skin; thereafter, after the slope changes, a further volume of water is injected into the skin, with the volume being determined as a function of the slope and of the pressure.

Figure 7:
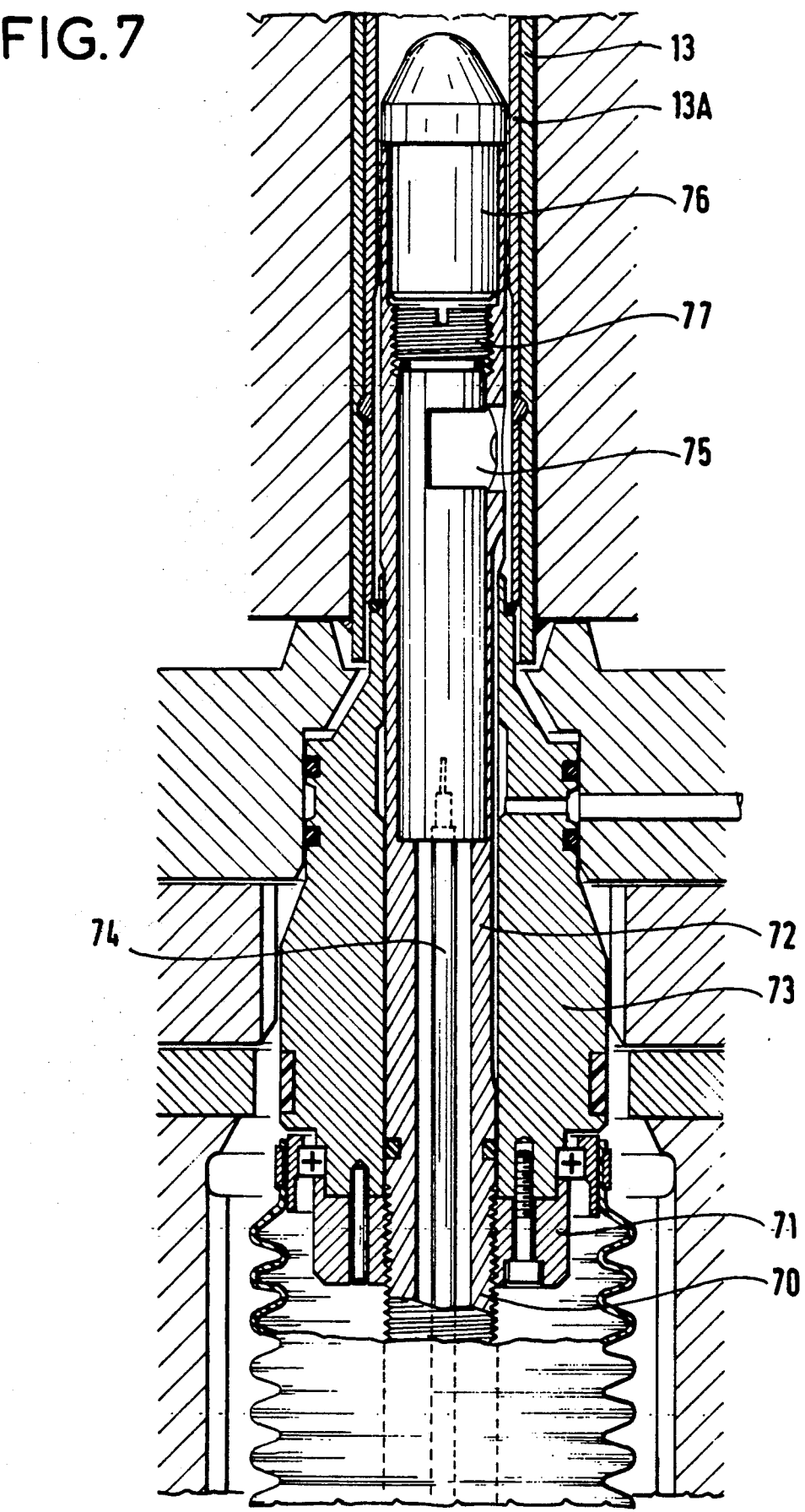
FIG. 7 is a fragmentary section through an ultrasonic weld monitoring lance.

FIG. 7 shows the lance for monitoring welds which is rotated by the pneumatic motor and which is moved axially by a threaded hollow screw 70 and nut 71 system. The lance itself 72 is disposed inside a bush 73. A coaxial cable 74 connected to an ultrasonic oscillator disposed in the vicinity of the push-pull device passes through the inside bore of the hollow screw 70 and connects to the ultrasound probe 75 which is connected to the conically-tipped probe head 76 by a nut 77. The interface echo between the sleeve 13A and the tube 13 is picked up, for example, every 1/100th of a turn by the probe on each turn of its helical displacement. The echoes as picked up can be used to make a diagram of the interface of the welded zone and the outside surface of the tube to be repaired in said zone.

FIGS. 8A and 8B show a tube expansion tool having inclined rollers for providing final expansion of the sleeve inside the tube. It comprises a spring 80 for keeping the drive square 81 connected to a drive cable away from the cage 82 so as to put the wheels in the minimum circumscribed diameter position. After the tube expansion tool has been put into place inside the sleeve and inside the motorized drive unit, the spring is compressed by the thrust cable. The tool includes a flexible longitudinal rod 83 of thermoplastic material such as a polyamide-imide, surrounded by a sheet 84 of plastic material such as a polyamide and provided at its rear end with an abutment 85 surrounding an abutment nut 86. For flexible tools, the abutment bears against the end of the sleeve to be inserted into the tube. The flexible tube 87 is extended by a steel spindle 83, lying inside a tempered steel cage 82. The jaw for driving the rod is provided with fluting enabling it to be rotated by the fluted hub of the pneumatic motor, and it is free to move axially by sliding in the fluting.

Figure 9:
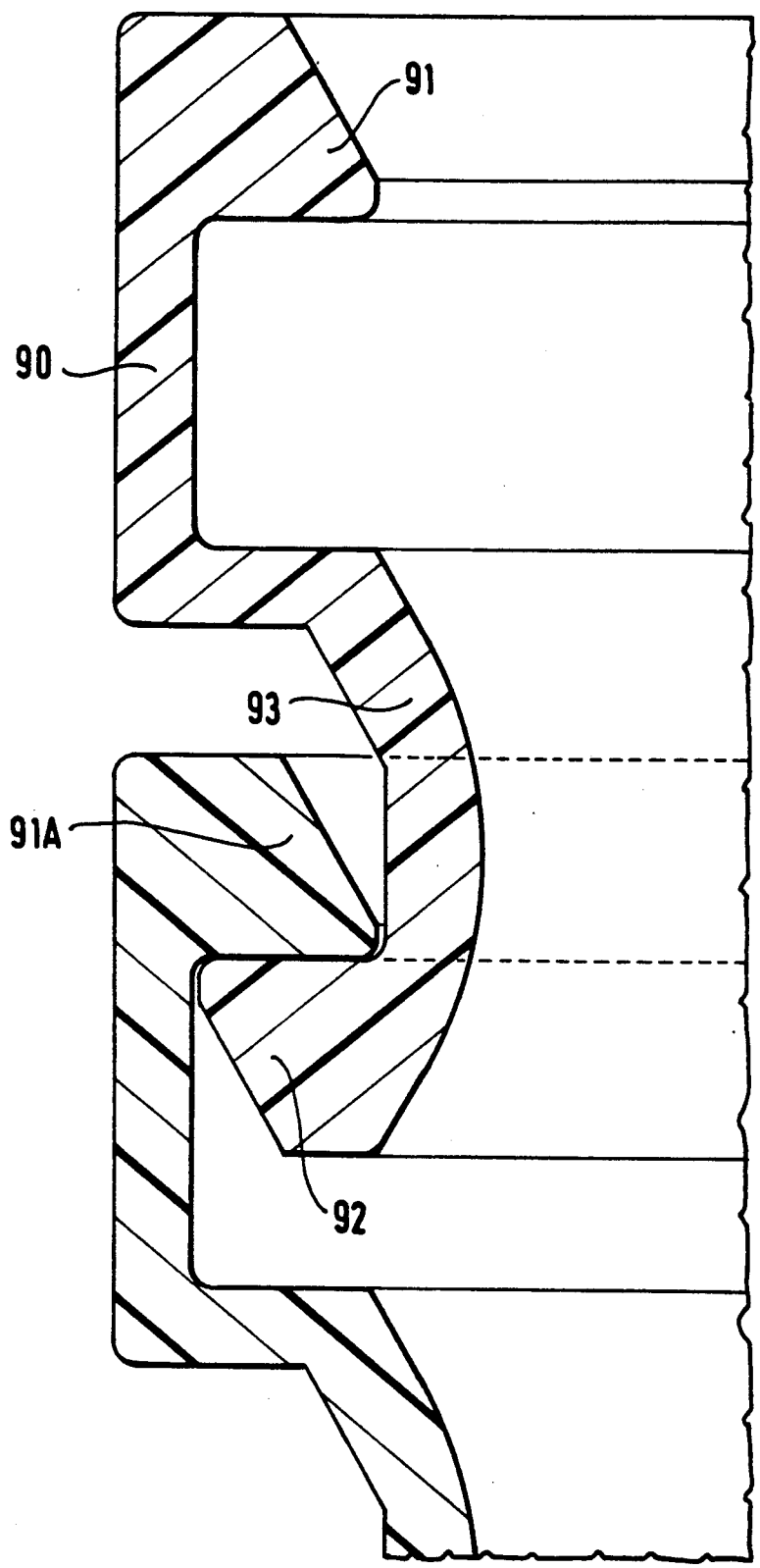
FIG. 9 is a section through a component having interfitting ends for constituting a flexible tube for inserting tools into the water box.

FIG. 9 shows that an element of the flexible tube (e.g. made of polyamide) comprises a cylindrical portion 90 having one end with an inside chamfer 91 that fixes in a flexible groove 93 at the opposite end of the element, said groove being fitted with an outside chamber 92. Adjacent elements are interconnected by engaging the outside chamber 92 of one element into the inside chamber 91A of the next element.

FIG. 10 shows an alternative flexible tube element which may also be made of polyamide, and which is constituted by a thin-walled mid cylindrical portion 101 connected at one end to a thin-walled spherically-shaped female end 102 provided with longitudinal slots 103, and at its other end to a thicker-walled male end 104 whose outside profile is likewise cylindrical in shape. Interconnection of two adjacent elements if facilitated by the elastic deformation capabilities imparted to the female end 102 of one element by its longitudinal slots as said end is engaged over the lower end of the adjacent element. A plastic ring 105 is then put into place to prevent the slots from splaying out again.

Flexible tubes built up from elements as shown in FIG. 9 or in FIG. 10 are very flexible and can reach the ends of any of the tubes of a tube plate, even those close to the periphery thereof, running from the push-pull device and going through the manhole of the water box.

We claim:

1. A machine for remotely lining the inside of a heat exchanger tube end with a sleeve within a heat exchanger, said heat exchanger comprising a tube plate supporting a plurality of tubes, each tube having a tube end, each said tube end being mounted in said tube plate of said heat exchanger with a water box being disposed beneath the tube plate, the water box being accessible from the outside via a manhole, the machine operating by a method including inserting a sleeve into each tube end, diametrically expanding the sleeve in a zone inside the tube plate and in a zone beyond the tube plate, then expanding the sleeve by rolling and then welding the sleeve in each of the expansion zones, said machine comprising a push-pull device outside the water box, with a flexible tube connecting the push-pull device to a motorized unit driving sleeve-fixing tools, a tool loader at a head of a cable driven by the push-pull device, and means for bringing an end of the flexible tube level with the tube end of each of said tubes in succession, and wherein the motorized unit for driving the tools comprises two superposed fluted hubs one hub being driven by a low speed electric motor and the other hub being driven by a pneumatic motor having a high speed of rotation.

2. A machine according to claim 1, wherein the pneumatic motor is mounted on a bearing and is provided with a force cell for measuring its couple.

3. A machine according to claim 1, wherein the sleeve fixing tools include tools for tube expansion by rolling driven by the fluted hub of the pneumatic motor engaging fluted drive jaws on spindles thereof, and having flutes therein allowing a jaw to slide axially.

4. A machine according to claim 3, wherein the sleeve-fixing tools include tools for tube expansion by rolling provided with springs for maintaining said spindles in a position clearly separated from a tool cage when at rest, and a thrust cable for compressing said springs.

5. A machine according to claim 1, wherein said sleeve-fixing tools include a tool for cleaning the inside of a tube comprising a flexible brush rotated by the pneumatic motor and moveable in translation via a nut and screw system including a screw provided with a central bore through which particles detached by the brush may be sucked, and said flexible brush being provided with an internal passage for effecting removal of said particles.

6. A machine according to claim 1, wherein the sleeve-fixing tools include a tool for placing the sleeve inside the tube having a skin of plastic material which is inflatable under the effect of hydraulic pressure in an internal chamber thereof.

7. A machine according to claim 6, wherein the skin is carried by a support having a retractable cone provided with a contact for detecting that the sleeve is in the proper position inside said tube.

8. A machine according to claim 6, wherein the skin is connected to a metering pump for delivering very small volumes and to means for comparing the increase in pressure after each pump stroke with the increase after preceding pump strokes.

9. A machine according to claim 1, wherein said sleeve-fixing tools include a tool for docking the sleeve against the tube inside the tube plate, said docking tool comprising a tube expander having rollers parallel to a spindle thereof, being provided with a projection for localized deformation of the sleeve, and wherein said pneumatic motor is coupled to said spindle via a screw and nut system.

10. A machine according to claim 1, wherein said sleeve-fixing tools include a tool for docking the sleeve against the tube beyond the tube plate, said docking tool comprises a tube expander having sloping rollers.

11. A machine according to claim 1, wherein said sleeve-fixing tools include tools for welding the sleeve to the tube having flexible lances driven in rotation by said electric motor and being connected to ducts for feeding said ducts with water, gas, and electricity, said ducts running inside a thrust cable.

12. A machine according to claim 1, including cells located close to the motorized unit for driving the tools and serving to detect the presence of the tools and to count the numbers of rotations of the tools.

13. A machine according to claim 1, including ultrasonic probes for monitoring a weld, said probes being rotated by the pneumatic motor and being moved axially by a screw and nut system connected to the pneumatic motor, said tools serving to pick up the interface echoes between the sleeve and the tube and the background echo on the tube.

14. A machine according to claim 1, wherein said flexible tube is constituted by an assembly of cylindrical elements having ends which interfit in one other.

15. A machine according to claim 1, wherein said flexible tube is constituted by an assembly of interfitting elements having ball-and-socket forming ends.

* * * * *